United States Patent [19]

Kuriyama et al.

[11] Patent Number: 4,476,314

[45] Date of Patent: Oct. 9, 1984

[54] PROCESS FOR PRODUCING OLEFIN OXIDES

[75] Inventors: Yasuhisa Kuriyama, Tokyo; Minoru Kakuda, Chiba; Shoichi Nitoh, Tokyo, all of Japan

[73] Assignee: Mitsubishi Gas Chemical Co., Inc., Tokyo, Japan

[21] Appl. No.: 415,196

[22] Filed: Sep. 7, 1982

[30] Foreign Application Priority Data

Sep. 4, 1981 [JP] Japan .................................. 56-139502
Nov. 26, 1981 [JP] Japan .................................. 56-189709

[51] Int. Cl.$^3$ .................. C07D 301/12; C07D 301/14
[52] U.S. Cl. ...................................... 549/531; 549/526
[58] Field of Search ............................ 549/531, 526

[56] References Cited

U.S. PATENT DOCUMENTS

| | | | |
|---|---|---|---|
| 2,870,171 | 1/1959 | Gable | 549/531 |
| 3,806,467 | 4/1974 | Watanabe et al. | 549/531 |
| 3,953,480 | 4/1976 | Delavarenne et al. | 549/531 |
| 4,026,908 | 5/1977 | Pralus et al. | 549/531 |
| 4,303,587 | 12/1981 | Schirmann et al. | 549/531 |

FOREIGN PATENT DOCUMENTS 1108197 6/1961 Fed. Rep. of Germany .
2803757 8/1978 Fed. Rep. of Germany .
2300765 9/1976 France .

OTHER PUBLICATIONS

M. Tsutsui, "Fundamental Research in Homogeneous Catalysis", vol. 3, (1979), pp. 327–343, (Chapter by M. Pralus et al., entitled New Ways in the Catalytic Epoxidation of Olefins by Hydrogen Peroxide).

*Primary Examiner*—Norma S. Milestone
*Attorney, Agent, or Firm*—Sughrue, Mion, Zinn, Macpeak and Seas

[57] ABSTRACT

A process for producing olefin oxides comprising epoxidizing olefins with hydrogen peroxide in the presence of an inorganic or organic antimony compound or organotin compound as a catalyst is disclosed.

6 Claims, No Drawings

PROCESS FOR PRODUCING OLEFIN OXIDES

FIELD OF THE INVENTION

The present invention relates to a process for producing olefin oxides and, more specifically, to a process for epoxidizing olefins with hydrogen peroxide in the presence of an antimony compound or an organotin compound as a catalyst.

BACKGROUND OF THE INVENTION

Olefin oxides have been used for various utilities in chemical industries. For example, olefin oxides have been used as intermediates for producing urethanes, glycol solvents, coating compositions, molding materials, surface active agents, plasticizers, and other products, and they have been produced by various processes.

Typical conventional processes for producing olefin oxides by epoxidation of olefins include the following three processes. The first process is a so-called "chlorohydrin process" and comprises reacting an olefin with chlorine or sodium hypochlorite in an alkaline medium to form chlorohydrin and subjecting chlorohydrin to dehydrochlorination to obtain an epoxide. The second process comprises air-oxidizing a hydrocarbon to form a hydroperoxide and epoxidizing an olefin with the hydroperoxide in the presence of a catalyst. This second process has a problem that a large amount of an alcohol is formed as a by-product from the hydroperoxide. The third process comprises air-oxidizing acetaldehyde to form peracetic acid, and epoxidizing an olefin with the peracetic acid. The third process also has a problem that a large amount of acetic acid formed as a by-product should be recovered.

In recent years, epoxidation of olefins by hydrogen peroxide has been proposed, and there are many reports on a process for producing olefin oxides which comprises reacting an olefin with hydrogen peroxide in an organic solvent in the presence of various types of epoxidation catalysts. The epoxidation catalysts used in these reports are mainly molybdenum and tungsten catalysts. These catalysts have a high catalytic activity, but they have a problem that they easily decompose hydrogen peroxide. Boron and arsenic catalysts have also been reported as catalysts having an epoxidation ability without causing such decomposition of hydrogen peroxide. However, the boron catalysts generally have a relatively low catalytic activity and the arsenic catalysts have a disadvantage in view of their high toxicity even though they have a relatively high catalytic activity, and, therefore, these catalysts are not satisfactory for practical use in industry.

Further, a process for epoxidation using a catalyst comprising an antimony compound and molybdenum or tungsten (Japanese Patent Publication No. 19216/80), or an organotin compound and molybdenum or tungsten (Japanese Patent Publication Nos. 25046/72 and 25323/72) has been proposed. Such catalyst has a relatively high catalytic activity, but it is still unsatisfactory in its low selectivity and reaction efficiency of hydrogen peroxide. As a result of extensive studies on epoxidation of olefins in the light of the above conventional disadvantages, the present inventors found catalysts comprising an antimony compound or an organotin compound having a high activity and a high selectivity and reached the present invention.

SUMMARY OF THE INVENTION

The present invention provides a process for producing olefin oxides which comprises directly epoxidizing an olefin with hydrogen peroxide by contacting the olefin with hydrogen peroxide in a liquid phase in the presence of an antimony compound catalyst or an organotin compound catalyst.

An object of the present invention is to provide novel catalysts having a high catalytic activity which makes it possible to perform epoxidation of olefins effectively with a high selectivity.

Other objects and advantages will be apparent from the following descriptions.

DETAILED DESCRIPTION OF THE INVENTION

In the present invention, the catalysts having a high catalytic activity which produce effectively olefin oxides with a high selectivity comprise an antimony compound or an organotin compound hereinafter described in detail. The antimony compound or the organotin compound used as a catalyst in the present invention does not substantially contain other metals such as molybdenum, tungsten or vanadium, etc.

Olefins to be epoxidized by the process of this invention are olefinically unsaturated hydrocarbon compounds and include substituted or unsubstituted straight chain or cyclic olefins. Generally, these olefins contain 2 to 20 carbon atoms and at least one double bond. Such olefins can be represented by the following formulae:

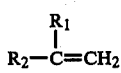

wherein $R_1$ and $R_2$, which may be the same or different, each represents hydrogen or a substituted or unsubstituted straight chain or branched chain alkyl group having 1 to 20 carbon atoms;

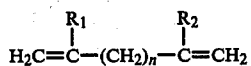

wherein $R_1$ and $R_2$ are as defined above, and n is 0 or an integer of 1 to 10;

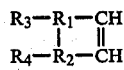

wherein $R_1$ and $R_2$, which may be the same or different, each represents an alkyl group having 1 to 4 carbon atoms, and $R_3$ and $R_4$, which may be the same or different, each represents hydrogen or a substituted or unsubstituted straight chain or branched chain alkyl group having 1 to 10 carbon atoms. These cyclic olefins have up to 10 carbon atoms and an unsaturated bond in the cyclic moiety thereof and are substituted by one or two alkyl groups having 1 to 10 carbon atoms;

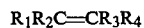

wherein $R_1$ and $R_3$, which may be the same or different, each represents a straight chain or branched chain alkyl group having 1 to 10 carbon atoms and $R_2$ and $R_4$ each represents hydrogen or the same group as that of $R_1$ and $R_3$; and

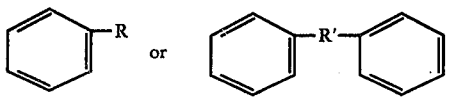

wherein R represents a monovalent alkenyl group having 2 to 10 carbon atoms, and R' represents a divalent alkenyl group having 2 to 5 carbon atoms.

Typical examples of olefins represented by the above formulae include aliphatic olefins such as propylene, butene, isobutene or hexene; cycloolefins such as cyclopentene, cyclohexene or cyclooctene; alkyl- or alkenylcycloolefins such as methylcyclohexene, methylcyclopentene or vinylcyclohexene; alkenyl aromatic hydrocarbons such as styrene, vinylbenzene or methylstyrene; conjugated or non-conjugated diolefins such as 1,5-cyclooctadiene, 1,5,9-cyclodecatriene, 1,4-cyclohexadiene or butadiene; olefinic alcohols such as allyl alcohol, methylvinylcarbinol or cyclohexanol; halogenated olefins such as allyl chloride or allyl bromide; and unsaturated aliphatic acids and esters thereof such as acrylic acid, methacrylic acid, crotonic acid, oleic acid, allyl acetate, soybean oil or linseed oil, etc.

The antimony compound catalyst used in the present invention comprises an inorganic antimony compound, an organic antimony compound or a mixture thereof.

The inorganic antimony compounds include oxides, oxyacids, oxyacid salts, oxyacid esters, halides, oxyhalides and sulfides of antimony. Examples of such inorganic antimony compounds are $Sb_2O_3$, $Sb_2O_4$, $Sb_2O_5$, $Sb(OH)_3$, $H[Sb(OH)_6]$, $NaSbO_2$, $KSbO_2$, $K_3SbO_4$, $SbCl_3$, $SbBr_3$, $Sb_4O_5Cl$, $SbOCl$, $Sb_2S_3$ and $Sb_2S_5$, etc.

The organic antimony compounds include compounds represented by the general formula RSbXY (when the valence of antimony is +3) wherein R represents an alkyl group having 1 to 12 carbon atoms, an aralkyl group having 7 to 12 carbon atoms or an aryl group having 6 to 12 carbon atoms, and X and Y each represents hydrogen, an alkyl group having 1 to 12 carbon atoms, an aralkyl group having 7 to 12 carbon atoms, an aryl group having 6 to 12 carbon atoms, a halogen atom, a hydroxyl group, an alkoxy group having 1 to 12 carbon atoms, an acyloxy group having 1 to 12 carbon atoms, —SbR'R", —OSbR'R", —NR'R", —PO(OR')$_2$, —OSiR'R"R''' or —S, wherein R', R" and R''' each represents an alkyl group having 1 to 12 carbon atoms, an aralkyl group having 7 to 12 carbon atoms or an aryl group having 6 to 12 carbon atoms.

Additional examples of organic antimony compounds are stibonic acid anhydrides represented by the formula (RSb=O)$_n$, wherein R is as defined above, and n represents a number of the recurring unit in the polymer structure; heterocyclic derivatives such as stiboran represented by the formula

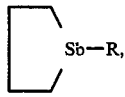

wherein R is as defined above; and antimony derivatives represented by the formula (RSb=)$_2$, wherein R is as defined above.

Examples of organic antimony compounds wherein the valency of antimony is +5 are those represented by the formulae R'R"R'''SbXY, R'R"Sb(=O)X and R'''Sb(=O)XY, wherein R', R", R''', X and Y are as defined above.

Specific examples of the above organic antimony compounds include $CH_3SbCl_2$, $C_6H_5SbCl_2$, $(CH_3)_2SbCl$, $(CH_3)_4SbCl$, $(C_6H_5)_2SbCl_2$, $(C_2H_5)_2SbOCH_3$, $(C_6H_5)_4SbOH$,

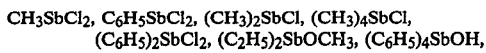

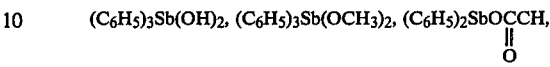

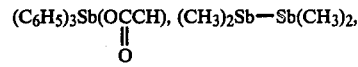

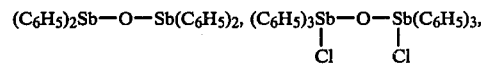

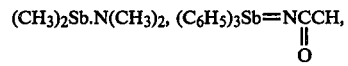

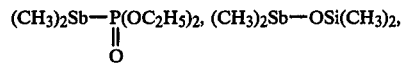

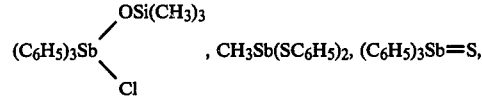

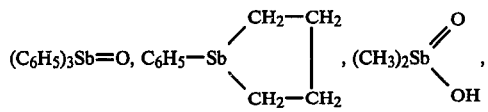

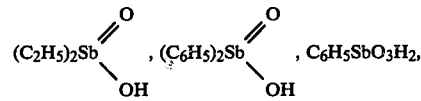

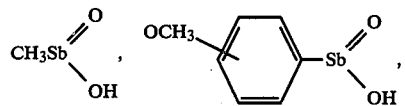

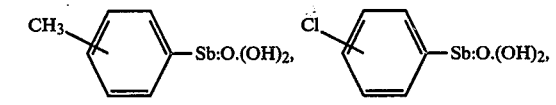

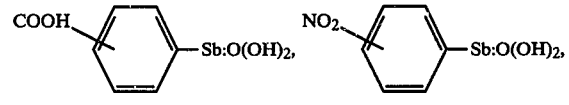

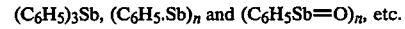

$(C_6H_5)_3Sb$, $(C_6H_5.Sb)_n$ and $(C_6H_5Sb=O)_n$, etc.

Of these antimony compounds, preferred compounds are those represented by the formulas R'R"Sb(=O)X and R'''Sb(=O)XY, and particularly preferred compounds are organic stibonic acids and organic stibinic acids represented by the formulas R'R"Sb(=O)OH and R'''Sb(=O)(OH)$_2$. Examples of such compounds are methylstibonic acid $(CH_3Sb\begin{smallmatrix}\diagup O\\ \diagdown (OH)_2\end{smallmatrix})$, phenylstibonic acid (C$_6$H$_5$.Sb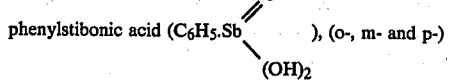), (o-, m- and p-)

methylphenylstibonic acids (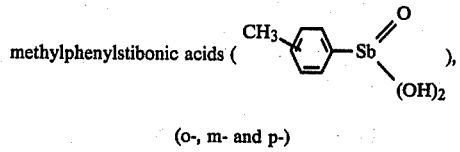), (o-, m- and p-)

methoxyphenylstibonic acids (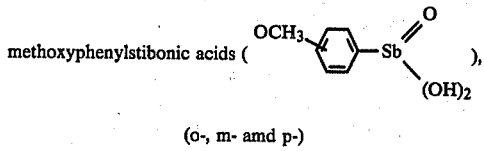), (o-, m- amd p-)

carboxyphenylstibonic acids (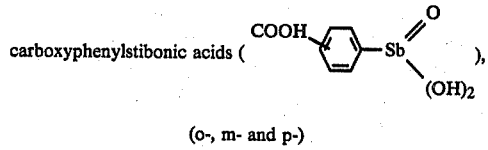), (o-, m- and p-)

chlorophenylstibonic acids (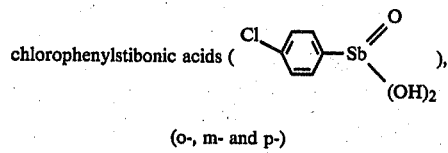), (o-, m- and p-)

nitrophenylstibonic acids (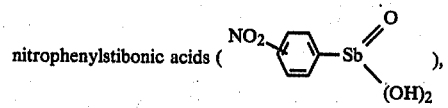), (o-, m- and p-)

dimethylstibinic acid ((CH$_3$)$_2$Sb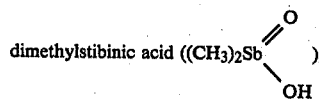), diethylstibinic acid ((C$_2$H$_5$)$_2$Sb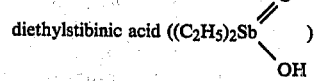)

and diphenylstibinic acid ((C$_6$H$_5$)$_2$Sb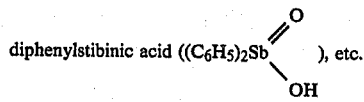), etc.

The organotin compounds used in the present invention include compounds represented by the general formulae RSnXYZ, RSn(=O)X and RR'Sn, wherein R and R' each represents an alkyl group having 1 to 12 carbon atoms, an aralkyl group having 7 to 12 carbon atoms or an aryl group having 1 to 12 carbon atoms, and X, Y and Z each represents hydrogen, an alkyl group having 1 to 12 carbon atoms, an aralkyl group having 7 to 12 carbon atoms, an aryl group having 6 to 12 carbon atoms, a halogen atom, a hydroxyl group, an alkoxy group having 1 to 12 carbon atoms, an acyloxy group having 1 to 12 carbon atoms, —SnR'R"R'", —OSnR'R"R'", —NR'R", —OSiR'R"R'" or —S—, wherein R', R" and R'" each represents an alkyl group, an aralkyl group or an aryl group as defined above.

Examples of the above organotin compounds are (C$_2$H$_5$)$_4$Sn, (C$_6$H$_5$)$_4$Sn, CH$_3$SnCl$_3$, C$_6$H$_5$SnCl$_3$, (C$_4$H$_9$)$_2$SnCl$_2$,

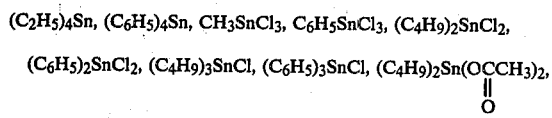

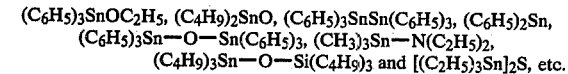

(C$_6$H$_5$)$_3$SnOC$_2$H$_5$, (C$_4$H$_9$)$_2$SnO, (C$_6$H$_5$)$_3$SnSn(C$_6$H$_5$)$_3$, (C$_6$H$_5$)$_2$Sn, (C$_6$H$_5$)$_3$Sn—O—Sn(C$_6$H$_5$)$_3$, (CH$_3$)$_3$Sn—N(C$_2$H$_5$)$_2$, (C$_4$H$_9$)$_3$Sn—O—Si(C$_4$H$_9$)$_3$ and [(C$_2$H$_5$)$_3$Sn]$_2$S, etc.

Of these organotin compounds, preferred compounds are those represented by the formula RSn(=O)X, and particularly preferred compounds are organic stannoic acids represented by the formula RSn(=O)OH. Specific examples of these organotin compounds are methylstannonic acid

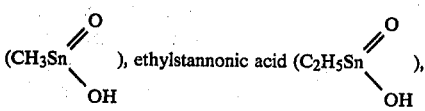, ethylstannonic acid (C$_2$H$_5$Sn...OH), butylstannonic acid 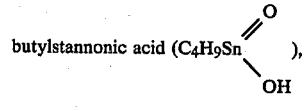, octylstannonic acid 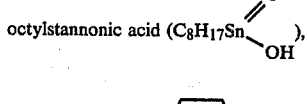, phenylstannonic acid (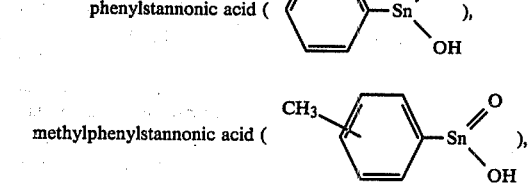), methylphenylstannonic acid (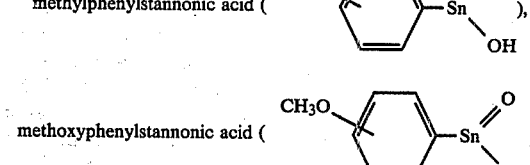), methoxyphenylstannonic acid (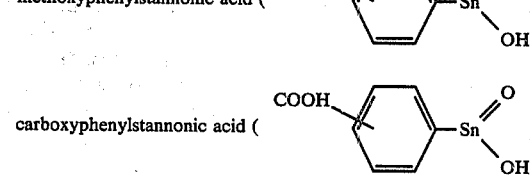), carboxyphenylstannonic acid (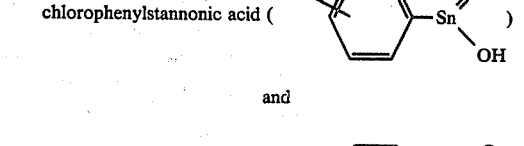), chlorophenylstannonic acid (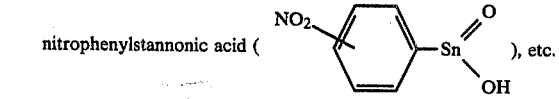)

and nitrophenylstannonic acid (...), etc.

It is preferred that the antimony compounds and the organotin compounds used as the catalysts in the present invention are soluble or partially soluble in the reaction system. From this standpoint, the organic antimony compounds or organotin compounds are preferred in the above described compounds. However, sparingly soluble or insoluble compounds can be used as well. Further, conventional technique for achieving sufficient contact of the reactants with the catalyst can be used in the present invention. For example, the catalyst can be supported on an inert carrier such as silica, alumina and the like.

In the present invention, it is preferred to conduct the reaction using a reaction solvent. Any solvent which can maintain the reaction system in a liquid state and is inactive to the reactants and the catalyst can be used. Generally, the reaction solvent can be suitably selected from alcohols, esters, ethers, saturated hydrocarbons, halogenated hydrocarbons, aromatic hydrocarbons and organic carboxylic acids, etc. Examples of the solvents include n-propanol, iso-propanol, n-butanol, isobutanol, t-butanol, amyl alcohol, cyclohexanol, ethylene glycol, propylene glycol, ethyl ether, isopropyl ether, dioxane, tetrahydrofuran, ethylene oxide, methyl acetate, ethyl acetate, phenyl acetate, cyclohexyl acetate, n-pentane, cyclohexane, cyclohexene, dichloromethane, dichloroethane, dichloropropane, tetrachloroethane, benzene, toluene, xylene, chlorobenzene, dichlorobenzene, acetic acid, propionic acid, butyric acid, isobutyric acid and benzoic acid, etc. Of these solvents, particularly preferred solvents are organic carboxylic acids and mixtures of the organic carboxylic acid and other solvents. Examples of these solvents or solvent systems are acetic acid, propionic acid, butyric acid, isobutyric acid, acetic acid-benzene, acetic acid-dichloromethane, acetic acid-dichloroethane, acetic acid-dichloropropane, propionic acid-benzene, propionic acid-cyclohexane, propionic acid-dichloromethane, propionic acid-dichloroethane, propionic acid-dichloropropane, propionic acid-t-butanol, propionic acid-methyl acetate, propionic acid-dioxane, and m-chlorobenzoic acid-dioxane, etc. With respect to the solvent, the type of solvents used (e.g., whether the organic acids alone or in combination with other solvents) or the ratio of the solvents can be suitably determined by taking consideration of the type of the olefins used for the reaction, the type of epoxides produced, ease of operation or economy, etc. For example, if the epoxide produced is easily ring-opened by an organic carboxylic acid, the ring opening reaction can be avoided or minimized by reducing a proportion of the organic carboxylic acid in the solvent. When the organic carboxylic acid is used in combination with other types of solvents, a preferred proportion of the carboxylic acid used is 1% or more, preferably 5% or more (by volume), based on the total volume of the liquid phase in the reaction system.

In the present invention, it is preferred to use hydrogen peroxide in the reaction at a concentration that the reactants other than the catalysts are maintained in a phase as uniform as possible under the reacting condition. Accordingly, a hydrogen peroxide aqueous solution having a concentration of about 30 to about 90% (by weight) is generally used. However, in some instances, hydrogen peroxide having higher concentrations may be required because some olefins easily cause ring opening by moisture in the reaction system. In such a case, it is preferred to perform the reaction while removing water from the reaction system by azeotropic distillation with the reaction solvent or while removing water out of the reaction system by continuously introducing an inert gas such as nitrogen, argon or helium into the reactor, or to use a process comprising removing water by adding a dehydrating agent such as anhydrous sodium sulfate or anhydrous magnesium sulfate, etc. to the reaction system.

The reaction temperature can be selected widely depending upon activity of the catalyst used, reactivity of the olefin used, easiness of ring-opening of the formed epoxy compounds or the type of the solvent selected, but it is generally in the range of about 0° C. to about 150° C., preferably 40° to 120° C. The reaction time can be generally about 5 minutes to 240 minutes. Further, the reaction can be carried out under atmospheric pressure or a pressurized condition so long as the reaction system can be maintained in a liquid phase. Generally a pressure of 1 to 150 atm. is preferably used.

The concentration of the catalyst used in the present invention can be selected fairly widely, and a concentration at which the catalyst exhibits a preferred catalytic activity can be suitable selected according to the type of the antimony compound or the organotin compound used as the catalyst, the type and the reactivity of olefin used, etc. Accordingly, the catalyst is used in an amount required for providing a catalytic activity, which is generally 1/2000 to ½ mol, preferably, 1/400 to 1/5 mol per mol of hydrogen peroxide. Further, the concentration of olefin in the reaction system is not critical, but it can be generally used in a molar ratio (olefin to hydrogen peroxide) of about 1/30 to 30/1.

In addition, it is desirable to add a stabilizer, for example, a chelating agent such as ethylenediaminetetraacetic acid, diethylenetriaminepentaacetic acid, cyclohexanediaminetetraacetic acid, aminotrimethylenephosphonic acid, 1-hydroxyethylidene-1,1-diphosphonic acid, ethylenediaminetetramethylenephosphonic acid (for example, Dequest 2041, a tradename of Monsanto Co.) and the like, etc., because the hydrogen peroxide reactant is relatively unstable and easily decomposed during the reaction by contamination with heavy metals, etc. thereby reducing the yield of the desired olefin oxides.

As described above, the process of the present invention is a remarkably advantageous in practicing on an industrial scale because epoxidation of olefin with hydrogen peroxide can be carried out in a high yield and a high selectivity by using the antimony compound or the organotin compound as the catalyst.

The present invention is illustrated in greater detail by the following examples.

EXAMPLE 1

A stainless (SUS 316) autoclave having a capacity of 300 CC was charged with 25 ml of dichloromethane, 10 ml of t-butanol and 5 ml of propionic acid as a solvent system and 0.5 g of p-methoxyphenylstibonic acid as a catalyst. Then, 0.113 mol of 90% hydrogen peroxide and 0.40 mol of propylene were added to the autoclave and the mixture was allowed to react at 70° C. for 60 minutes. After completion of the reaction, unreacted hydrogen peroxide was found to be 0.025 mol and, upon analysis by gas chromatography, the propylene oxide produced was found to be 0.074 mol. These results indicate that propylene oxide was produced in a selectivity of 84% and a conversion of 77%, based on the amount of hydrogen peroxide used.

EXAMPLE 2

A four-necked flask having a capacity of 100 CC equipped with a water separator and a reflux condenser was charged with 15 ml of dioxane and 10 ml of acetic acid as a solvent system and 0.5 g of phenylstibonic acid as a catalyst. Then, 40 ml of cyclohexene was added thereto and the mixture was heated at reflux. Then, 0.104 mol of 60% hydrogen peroxide was added dropwise over 30 minutes with stirring. After completion of the addition, the reaction was carried out under refluxing for 30 minutes. After completion of the reaction, unreacted hydrogen peroxide was found to be 0.011 mol and, upon analysis by gas chromatography, the cyclohexene oxide produced was found to be 0.086 mol. These results indicate that cyclohexene oxide was produced in a selectivity of 92% and a conversion of 89%, based on the amount of hydrogen peroxide used.

EXAMPLE 3

A stainless (SUS 316) autoclave having a capacity of 300 CC was charged with 25 ml of benzene and 15 ml of t-butanol as a solvent system and 0.5 g of p-chlorophenylstibonic acid as a catalyst. Then, 0.112 mol of 90% hydrogen peroxide and 0.40 mol of propylene were added to the autoclave and the mixture was allowed to react at 70° C. for 60 minutes. After completion of the reaction, unreacted hydrogen peroxide was found to be 0.088 mol and, upon analysis by gas chromatography, the propylene oxide produced was found to be 0.021 mol. These results indicate that propylene oxide was produced in a selectivity of 87% and a conversion of 21%, based on the amount of hydrogen peroxide used.

EXAMPLE 4

A 200 CC glass autoclave was charged with 200 ml of propionic acid and 20 ml of dichloromethane as a solvent system and 1.0 g of phenylstibonic acid as a catalyst. Then, 20 ml of allyl chloride, 0.02 g of a stabilizer (Dequest 2041, produced by Monsanto Co.) and 0.098 mol of 90% hydrogen peroxide were added to the autoclave and the mixture was allowed to react at 110° C. for 60 minutes with stirring. After completion of the reaction, unreacted hydrogen peroxide in the reaction solution was found to be 0.007 mol. Upon analysis of the products in the reacting solution by gas chromatography, the epichlorohydrin produced was found to be 0.076 mol which indicate that the epichlorohydrin was produced in a selectivity of 84% and a conversion of 93% based on the amount of hydrogen peroxide used.

EXAMPLE 5

A four-necked flask equipped with a reflux condenser was charged with 45 ml of propionic acid as a solvent and 0.5 g of antimony trichloride as a catalyst. Then, 20 ml of allyl chloride was added thereto and the mixture was refluxed with stirring. 0.100 mol of 60% hydrogen peroxide was added thereto and the mixture was allowed to react for 120 minutes under refluxing. After completion of the reaction, unreacting hydrogen peroxide was found to be 0.022 mol and, upon analysis by gas chromatography, the epichlorohydrin produced was found to be 0.060 mol. These results indicate that the epichlorohydrin was produced in a selectivity of 76% and a conversion of 78%, based on the amount of hydrogen peroxide used.

EXAMPLE 6

The reaction was conducted in the same manner as described in Example 5 but using 0.105 mol of 90% hydrogen peroxide. In this reaction, epichlorohydrin was produced in a selectivity of 75% and a conversion of 94%, based on the amount of hydrogen peroxide used.

EXAMPLE 7

The reaction was conducted in the same manner as described in Example 5 but using 0.5 g of triphenyl antimony as a catalyst and 0.104 mol of 90% hydrogen peroxide. In this reaction, epichlorohydrin was produced in a selectivity of 84% and a conversion of 88%, based on the amount of hydrogen peroxide used.

EXAMPLE 8

A four necked flask having a capacity of 100 CC equipped with a water separator and a reflux condenser was charged with 24 ml of propionic acid and 25 ml of dichloroethane as a solvent system and 1.0 g of diphenylstibinic acid as a catalyst. Then, 30 ml of allyl chloride was added thereto and the mixture was refluxed. 0.103 mol of 60% hydrogen peroxide was then added dropwise thereto over 30 minutes with stirring. After completion of the addition, the mixture was allowed to react for 120 minutes. During the reaction, water in the reaction system was removed by refluxing the reacting solution. After completion of the reaction, unreacted hydrogen peroxide was found to be 0.008 mol and the epichlorohydrin produced was found to be 0.088 mol. These results indicate that epichlorohydrin was produced in a selectivity of 93% and a conversion of 92%, based on the amount of hydrogen peroxide used.

EXAMPLE 9

A four-necked flask having a capacity of 100 CC equipped with a water separator and a reflux condenser was charged with 15 ml of t-butanol and 5 ml of propionic acid as a solvent system and 0.5 g of butylstannonic acid as a catalyst. Then, 50 ml of cyclohexene was added thereto and the mixture was refluxed. 0.103 mol of 90% hydrogen peroxide was then added dropwise thereto over 10 minutes with stirring. After completion of the addition, the mixture was allowed to react under refluxing for 30 minutes while removing water forming during the reaction by the water separator. After completion of the reaction, unreacted hydrogen peroxide was found to be 0.006 mol and, upon analysis by gas chromatography, the cyclohexene oxide produced was found to be 0.084 mol. These results indicate that cyclohexene oxide was produced in a conversion of 94% and a selectivity of 87%, based on the amount of hydrogen peroxide used.

EXAMPLE 10

A reaction was carried out in the same manner as described in Example 9 for 120 minutes using 20 ml of t-butanol. In this reaction, cyclohexene oxide was produced in a conversion of 47% and a selectivity of 40%, based on the amount of hydrogen peroxide used.

EXAMPLE 11

A 100 CC four-necked flask was charged with 45 ml of propionic acid as a solvent and 0.5 g of phenylstannonic acid as a catalyst. Then, 20 ml of allyl chloride was added thereto and the mixture was refluxed. 0.101 mol mol of 90% hydrogen peroxide was then added dropwise over 10 minutes with stirring. After completion of the addition, the mixture was allowed to react for 110 minutes under refluxing. After completion of the reaction, unreacted hydrogen peroxide was found to be 0.018 mol and, upon analysis by gas chromatography, the epichlorohydrin produced was found to be 0.077 mol. These results indicate that epichlorohydrin was produced in a conversion of 82% and a selectivity of 93%, based on the amount of hydrogen peroxide used.

EXAMPLE 12

A reaction was conducted in the same manner as described in Example 11 but using 0.5 g of diphenyltin oxide as a catalyst. In this reaction, epichlorohydrin was produced in a conversion of 80% and a selectivity of 94%, based on the amount of hydrogen peroxide used.

EXAMPLE 13

A 200 CC glass autoclave was charged with 20 ml of propionic acid and 20 ml of dichloroethane as a solvent system and 0.5 g of octylstannonic acid as a catalyst. Then, 20 ml of allyl chloride, 0.02 g of a stabilizer (Dequest 2041, produced by Monsanto Co.) and 0.101 mol of 90% hydrogen peroxide were added thereto and the mixture was allowed to react at 100° C. for 60 seconds with stirring. After completion of the reaction, unreacted hydrogen peroxide in the reacting solution was found to be 0.010 mol and, upon analysis of the products in the reacting solution by gas chromatography, the epichlorohydrin produced was found to be 0.082 mol. These results indicate that epichlorohydrin was produced in a conversion of 90% and a selectivity of 90%, based on the amount of hydrogen peroxide used.

EXAMPLE 14

A stainless (SUS 316) autoclave having a capacity of 300 CC was charged with 25 ml of dichloromethane, 10 ml of t-butanol and 5 ml of propionic acid as a solvent system and 0.5 g of butyl stannonic acid as a catalyst. Then, 0.102 mol of 90% hydrogen peroxide and 0.40 mol of propylene were added thereto and the mixture was allowed to react at 70° C. for 60 minutes. After completion of the reaction, unreacted hydrogen peroxide was found to be 0.029 mol and, upon analysis by gas chromatography, the propylene oxide produced was found to be 0.063 mol. These results indicate that propylene oxide was produced in a conversion of 72% and a selectivity of 86%, based on the amount of hydrogen peroxide used.

While the invention has been described in detail and with reference to specific embodiment thereof, it will be apparent to one skilled in the art that various changes and modifications can be made therein without departing from the spirit and scope thereof.

What is claimed is:

1. A process for producing an olefin oxide comprising reacting an olefin with hydrogen peroxide in a liquid phase in the presence of (a) a solvent comprising an organic carboxylic acid, wherein said organic carboxylic acid is present in an amount of 5% or more by volume based on the total volume of the liquid phase in the reaction system, and (b) a catalyst comprising at least one organotin compound represented by the formulae:

RSnXYZ, and

RSn(=O)X wherein R represents an alkyl group having 1 to 12 carbon atoms, an aralkyl group having 7 to 12 carbon atoms or an aryl group having 6 to 12 carbon atoms; X, Y and Z, which may be the same or different, each represents hydrogen, an aryl group having 6 to 12 carbon atoms, a halogen atom, a hydroxyl group, an alkoxy group having 1 to 12 carbon atoms, or an acyloxy group having 1 to 12 carbon atoms.

2. The process according to claim 1, wherein said organotin compound is selected from the group consisting of the compounds represented by the formula:

RSn(=O)X wherein R and X are as defined above.

3. The process according to claim 1, wherein said organotin compound is selected from the group consisting of the compounds represented by the formula:

TSn(=O)OH wherein R is as defined above.

4. The process according to claim 3, wherein said organotin compound is selected from the group consisting of ethylstannonic acid, butylstannonic acid, octylstannonic acid, phenylstannonic acid, methoxyphenylstannonic acid, carboxyphenylstannonic acid, chlorophenylstannoic acid and nitrophenylstannonic acid.

5. The process according to claim 1, wherein the organotin compound is used in an amount of 1/2000 to ½ mol per mol of hydrogen peroxide.

6. The process according to claim 1, wherein a molar ratio of said olefin to said hydrogen peroxide is 1/30 to 30/1.

* * * * *

UNITED STATES PATENT AND TRADEMARK OFFICE
CERTIFICATE OF CORRECTION

PATENT NO. : 4,476,314

DATED : October 9, 1984

INVENTOR(S) : Kuriyama et al

It is certified that error appears in the above-identified patent and that said Letters Patent is hereby corrected as shown below:

Claim 3, line 4 delete "TSn(=O)OH" and insert therefor --RSn(=O)OH--.

Signed and Sealed this

Fourteenth Day of May 1985

[SEAL]

Attest:

DONALD J. QUIGG

Attesting Officer

Acting Commissioner of Patents and Trademarks